United States Patent [19]

Leaseburge et al.

[11] Patent Number: 4,681,678
[45] Date of Patent: Jul. 21, 1987

[54] SAMPLE DILUTION SYSTEM FOR SUPERCRITICAL FLUID CHROMATOGRAPHY

[75] Inventors: Emory J. Leaseburge; Kenneth J. Melda, both of Lewisburg, W. Va.

[73] Assignee: Combustion Engineering, Inc., Windsor, Conn.

[21] Appl. No.: 917,628

[22] Filed: Oct. 10, 1986

[51] Int. Cl.⁴ .............................................. B01D 15/08
[52] U.S. Cl. ...................................... 210/101; 55/386; 210/198.2; 417/46; 417/401
[58] Field of Search ...................... 210/101, 198.2, 656, 210/659; 73/61.1 C; 55/386; 417/46, 401

[56] References Cited

U.S. PATENT DOCUMENTS

| | | | |
|---|---|---|---|
| 3,362,618 | 1/1968 | Fortinov | 417/401 |
| 3,839,863 | 10/1974 | Frazier | 417/401 |
| 3,963,383 | 6/1976 | Hill | 417/401 |
| 4,128,476 | 12/1978 | Rock | 210/198.2 |
| 4,347,131 | 8/1982 | Brownlee | 210/198.2 |
| 4,368,008 | 1/1983 | Budzich | 417/46 |
| 4,422,942 | 12/1983 | Allington | 210/101 |
| 4,478,720 | 10/1984 | Perrut | 210/198.2 |
| 4,487,080 | 12/1984 | Leaseburge | 73/863.83 |
| 4,580,759 | 4/1986 | Leaseburge | 137/625.48 |
| 4,592,842 | 6/1986 | Tomlinson | 210/198.2 |

Primary Examiner—Ernest G. Therkorn
Attorney, Agent, or Firm—William W. Habelt

[57] ABSTRACT

An apparatus for analyzing a process stream (1) via supercritical fluid chromatography including container means (10), extraction means (50) for drawing a known sample volume from the process stream and injecting the sample volume into a known volume of supercritical fluid to form a dilute mix (5), analyzer means (70) for analyzing the dilute mix via supercritical fluid chromatography, sample inlet valve means (60) for receiving the dilute mix from the extraction means (50) and supplying a portion of the dilute mix to the analyzer means (70), pneumatically driven piston-type pump means (30) for drawing the substance from the container means (10) and delivering same under pressure either to the extraction means (50) or to the analyzer means (70) as desired, and control means (40) for supplying low pressure air to the pump means (30) in a controlled manner so as to draw the substance from the container means (10) and maintain the substance at a desired pressure above the supercritical pressure for delivery to the analyzer means (70) and the extraction means (50) as desired.

1 Claim, 2 Drawing Figures

SAMPLE DILUTION SYSTEM FOR SUPERCRITICAL FLUID CHROMATOGRAPHY

BACKGROUND OF THE INVENTION

The present invention relates to supercritical fluid chromatography and, more particularly, to an apparatus for analyzing a process stream via supercritical fluid chromatography having improved sample extraction system for drawing a sample volume from a process stream and diffusing the sample volume in a volume of supercritical fluid carrier for delivery to the analyzing system.

Supercritical fluid chromatography is an analytical technology which permits the analysis of high molecular weight samples in a rapid and efficient manner. The supercritical state is the region above a substance's critical point, which is defined as the temperature and pressure at which the liquid and vapor phases of the substance exists in equilibrium with each other and become identical, forming a single phase. Above this critical point in temperature and pressure, the fluid has a viscosity close to that of a gas but the solubility of a liquid and therefore is uniquely suitable as a mobile phase for transporting a high molecular weight compound through very small diameter tubes and conduits in an analyzer such as a chromatograph. There are several substances which are well known as potential supercritical fluid phases including ammonia, pentane, isobutane, and carbon dioxide. A supercritical fluid is commonly obtained by pressurizing and heating a substance above its critical temperature and pressure.

Supercritical fluid chromatography using capillary columns requires a very small sample volume. Therefore, the sample to be analyzed can be diluted in a much larger volume of supercritical fluid. This dilution can be readily accomplished in the laboratory by diluting the sample volume with a solvent prior to passing the diluted sample to the chromatograph column. However, to provide on-line analysis of a process stream using supercritical fluid chromatography in an efficient manner, the sample preparation process must be automated. Prior attempts at automation of the dilution/sampling process has resulted in complex valving and pumping systems to mix the sample and solvents at known ratios.

SUMMARY OF THE INVENTION

It is an object of the present invention to provide an apparatus for sample dilution prior to analysis by an on-line supercritical fluid chromatograph.

An apparatus is provided for analyzing a process stream via supercritical fluid chromatography which consists of a container means containing a substance which can be converted to a supercritical fluid, extraction means for drawing a sample volume from the process stream and injecting the sample volume into the supercritical fluid to form a dilute mix, analyzer means for analyzing the dilute mix via supercritical fluid chromatography, sample inlet valve means for receiving the dilute mix from the extraction means and supplying a portion of the dilute mix to the analyzer means, pump means for receiving the supercritical fluid from the container means and delivering same either to the extraction means or to the analyzer means, and means for supplying low pressure air to the pump means in a controlled manner so as to pressurize the substance from the container means and maintain the substance at a pressure above the supercritical pressure for delivery to the analyzer means and the extraction means as desired.

The extraction means comprises a sample capture valve for drawing a sample of known volume from the process stream and a pneumatically driven pump wherein the known volume sample is diffused into a known volume of supercritical fluid to form a dilute mixture suitable for sampling. The pump has a first large diameter chamber, a second small diameter chamber extending axially therefrom, and an axially extending piston rod enclosed therebetween. The piston rod has a first large diameter head disposed and axially translatable in sealing relationship within the first chamber and a second small diameter head disposed and axially translatable in sealing relationship within the second chamber. Low pressure air is supplied to the first chamber of the pump so as to compress the supercritical fluid supplied to the second chamber to maintain the supercritical fluid at a desired pressure above the supercritical pressure while the sample volume is diffused into the supercritical fluid to form the dilute mix which is then transferred to the sample inlet valve.

BRIEF DESCRIPTION OF THE DRAWING

The present invention will be described hereinafter with reference to the accompanying drawing wherein.

DETAILED DESCRIPTION OF A PREFERRED EMBODIMENT

Figure 1:
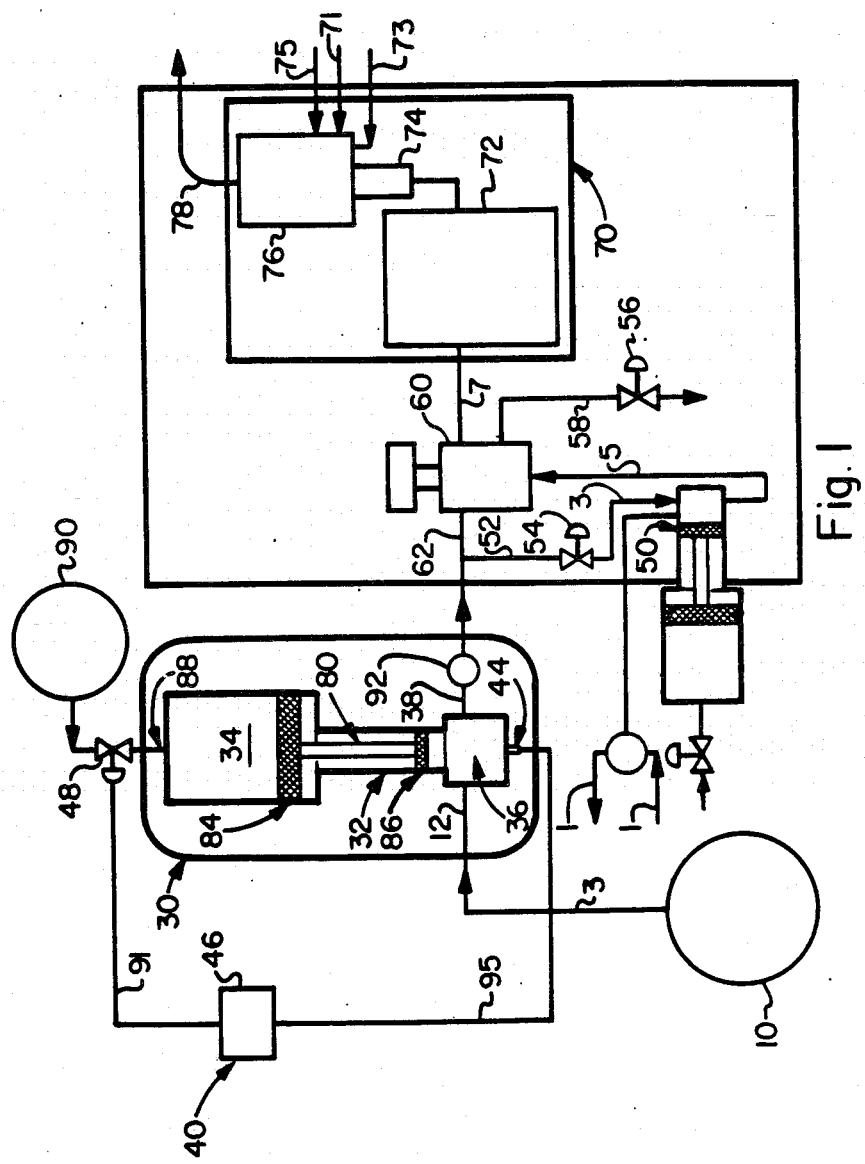
FIG. 1 is a schematic representation of a preferred embodiment of the apparatus of the present invention.

Referring now to FIG. 1, there is schematically depicted therein an apparatus for analyzing a process stream via supercritical fluid chromatography embodying the present invention. The primary components making up the apparatus of the present invention are container means 10 for providing a substance to be converted to a supercritical fluid, a supercritical fluid chromatograph 20 wherein the sample is prepared and analyzed, pump means 30 interconnected therebetween for drawing substance from the container means 10 and delivering it as a supercritical fluid to the chromatograph 20, and control means 40 for controlling the supply of low pressure air to the pump means.

In the best mode embodiment of the invention presently contemplated, the chromatograph 20 includes extraction system 50, sample inlet valve 60, and analyzer means 70. In operation, a sample volume is drawn from the process stream 1 and injected into a stream of supercritical fluid 3 via the extraction system 50 whereby the sample volume is diffused into the supercritical fluid to form a dilute mix 5 which is transferred to the sample inlet valve 60. A typical sample withdrawn from the process stream 1 via the extraction means 50 would have a volume of 1 microliter and would be introduced within the extraction means into a stream of supercritical fluid to produce a dilute mix of the sample volume diffused within the supercritical fluid. The supercritical fluid is supplied to the extractor means 50 through delivery line 52 by opening valve 54 as desired.

The dilute mix of the sample from the process stream 1 diffused in the supercritical fluid 3 passes from the extraction system 50 to sample inlet valve 60. The dilute mix passes through the sample inlet valve 60 and a fixed volume of the sample is passed to the analyzer means 70 to be analyzed via supercritical fluid chromatography.

The analyzer means 70 may constitute any of a number of known commercially available apparatus or the like for analyzing a sample by supercritical fluid chromatography. Although the exact composition of the analyzer means 70 is not critical to the present invention, it is presently contemplated that analyzer means 70 would include, as shown in the drawing, a column oven 72, a flame ionization detector 76 disposed downstream of the column oven 72 and interconnected therewith through interface means 74 to receive dilute mix sample to be analyzed from the column oven 72. The column oven 72 may be any suitable commercially available oven capable of heating the column which receives the dilute mixture from the sample inlet valve 60 to the temperature required for proper chromatographic separation.

Although a number of detectors could be utilized as the detector means 76, such as ultraviolet detectors, or infrared detectors, it is presently contemplated that detector means 76 comprise a flame ionization detector. The flame ionization detector 76 is of conventional design and is maintained a temperature above 300° C. to prevent the sample from condensing at the ambient pressure existing in the detector. Hydrogen gas 71 and nitrogen gas 73 are supplied to the flame ionization detector as fuel and dilution gas, respectively, together with combustion air 75 to produce a flame within the detector into which the dilute mix sample is passed through interface means 74 so that the species within the sample may be ionized for detection in accordance with conventional flame ionization detection techniques. The combustion products from the flame ionization detector are vented from the chromatograph 20 through vent line 78.

Interface means 74 is provided for delivery of the dilute mix from the column oven 72 into the detection means 74. The dilute mix of process sample dissolved in supercritical fluid exits the column located in the oven 72 at a pressure of about 7800 psi to pass into the ionization detector 76 which is maintained at ambient pressure conditions. The interface means 74 serves to dissipate the energy liberated during this transition from very high pressure to ambient pressure.

Preferably, the pump means 30 for receiving the substance from the container means 10 through supply line 12 and delivering the pressurized substance either to the extraction system 50 through a first delivery line 52 or to the sample inlet valve 60 through a second delivery line 62 comprises a pneumatically driven piston-type pump 32 having a first larger diameter chamber 34, a second smaller diameter chamber 36 extending axially from the larger diameter chamber 34, and an axially extended piston rod 80 enclosed and extending therebetween. The piston rod 80 has a first large diameter head 84 disposed and axially translatable in sealing relationship within the first chamber 34 and a second small diameter head 86 disposed and axially translatable in sealing relationship within the second chamber 36.

In operation, pressurized air from air supply 90, typically at a pressure of about 80 psi, is passed through control valve 48 and conduit 88 to the first larger diameter chamber 34 of the pump 32 to generate a force against the large diameter piston head 84 thereby causing the piston rod 80 to translate axially within the pump 34 thereby compressing the substance within the second smaller diameter chamber 36 of the pump 32 by movement of the small diameter head 86 on the opposite end of the piston rod 80. In this manner, the substance may be compressed to and maintained at a desired pressure which is above that substance's critical pressure. It can be supplied to the chromatograph 20 through outlet line 38 and filter 92 at desired rates. When the analysis is complete, the system is depressurized by venting the air from the first larger diameter chamber 34 of the pump means 80 thereby resulting in the piston rod 80 withdrawing axially from the second smaller diameter chamber 36 further into the larger diameter chamber 34 and simultaneously drawing additional chemical substance from the container means 10 through line 12 to refill chamber 36.

In order to facilitate supply of supercritical fluid to the chromatograph 20 at desired pressures, control means 40 is provided which comprises pressure transducer means 44 operatively associated with pump 32 to sense the pressure existing in the smaller diameter chamber 36 of the pump 32, a microprocessor 46, preferably programmable, adapted to receive a signal 95 from the pressure transducer 44, and flow control valve 48 disposed in the air supply conduit 88 for controlling the flow of air therethrough from air supply 90 in response to the signal 91 received from the microprocessor 46. The pressure transducer means 44 is mounted in the wall of the smaller diameter chamber 36 of the pump 32 to sense the pressure therein and send a continuous signal 95 indicative of the pressure within the chamber 36 to the microprocessor 46.

The microprocessor 46 processes the signal 95 and generates a signal 91 which is sent to flow control valve 48 to manipulate the control valve to increase or decrease the flow of pressurized air from the air supply 90 through the conduit 88 to the larger diameter chamber 34 of the pump 32 as a means of controlling the force exerted by the air pressure upon the piston head 84 within the larger diameter chamber 34 and therefore control the compression force exerted upon the substance within the smaller diameter chamber 36 at the opposite end of the pump 32. The microprocessor 46 is preferably programmable so that the operator may input any desired pressure at the control conditions against which the microprocessor 46 will process the pressure signal 95 received from the transducer means 44 and generate the control signal 91. The microprocessor can also be programmed to provide changes in the pressure in the chamber 36 over the period of analysis and time the venting and pressuring of the larger diameter chamber 34 so as to control the refilling and compressing of the substance in the smaller diameter chamber 36 and activate the supply of pressurized substance to the chromatograph 20.

Figure 2:
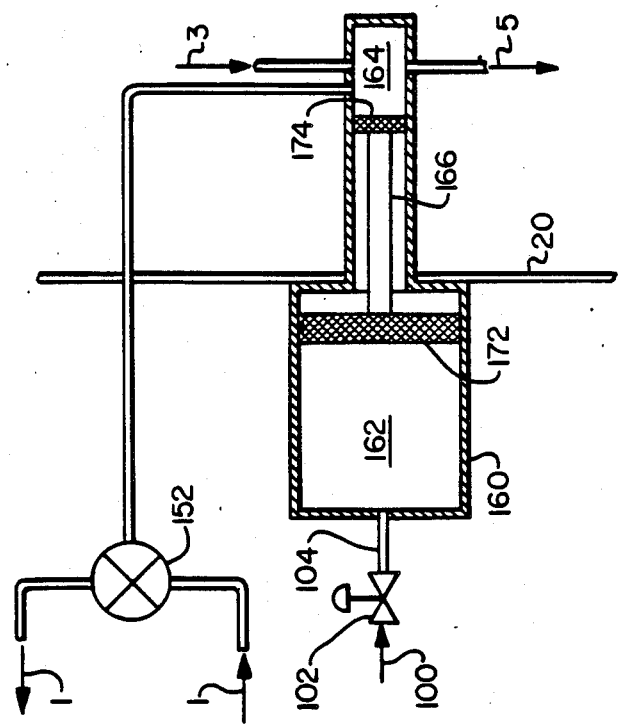
FIG. 2 is an enlarged schematic view of the extraction system employed in the apparatus of FIG. 1.

Referring now to FIG. 2, the extraction system 50 of the present invention comprises sample capture valve 152 and syringe pump 160. The sample capture valve 152 is activated to draw a sample of known volume from the process stream for injection into the syringe pump 160. The syringe pump 160 comprises a first larger diameter chamber 162, a second smaller diameter chamber 164 extending axially from the larger diameter chamber 162, and an axially extending plunger 166 enclosed and extending axially therebetween. The plunger 166 has a first large diameter head 172 disposed and axially translatable in sealing relationship within the first chamber 162 and a second small diameter head 174 disposed and axially translatable in sealing relationship within the second chamber 164.

In operation, shut-off valve 54 is opened and supercritical fluid 3 is injected from pump means 30 through delivery line 52 into the second small diameter chamber 164 of the syringe pump 160 at the desired supercritical pressure. The undiluted small controlled volume sample taken from the process stream in the sample capture valve 152 is then injected into the known controlled volume of supercritical fluid within the second small diameter chamber 164. Due to the high diffusity associated with supercritical fluid, the smaple is readily diffused therein and equilibrium is rapidly reached. The resultant dilute mix is then passed to the sample inlet valve by activating the syringe pump 160 and opening valve 56 to force the dilute mix out of the chamber 164 through the sample inlet valve 60.

Accordingly, the present invention provides an extraction system which can be rapidly cycled, which eliminates the need for solvents in diluting the sample, and which provides dilution of the sample prior to injection into the sample inlet valve. Additionally, the extraction system can be used in hazardous areas with supercritical carbon dioxide, which is non-volatile and non-toxic, being used as the mobile fluid as the pneumatically-driven system does not utilize any electrically operated valves.

We claim:

1. An apparatus for analyzing a process stream via supercritical fluid chromatography comprising:

a. chromatograph means for analyzing a sample of the process stream diluted in a volume of the supercritical fluid via supercritical fluid chromatography;

b. pump means for drawing a supercritical fluid substance from a container means through a supply line, pressurizing said supercritical fluid substance and delivering said pressurized supercritical fluid substance to said chromatograph means; and c. extraction means operatively associated with said chromatograph means for drawing a known sample volume from the process and injecting said volume into a known volume of supercritical fluid substance to form a dilute mix for analysis, said extraction means comprising a pneumatically driven syringe pump having a first larger diameter chamber adapted to receive pressurized air, a second smaller diameter chamber adapted to receive supercritical fluid substance from said pump means, and an axially extending plunger having a first large diameter head disposed and axially translatable in sealing relationship within the first chamber and a second small diameter head disposed and axially translatable in sealing relationship within the second chamber, and a sample capture valve for drawing a sample of known volume from the process stream and transferring said sample to the second smaller diameter chamber to diffuse in the supercritical fluid substance to form said dilute mix.

* * * * *